United States Patent [19]
Heruth et al.

[11] Patent Number: 5,713,858
[45] Date of Patent: Feb. 3, 1998

[54] PERMANENTLY IMPLANTABLE GUIDING CATHETER

[75] Inventors: Kenneth T. Heruth, Maple Grove; Scott Ward, South St. Paul, both of Minn.

[73] Assignee: Medtronic, Inc., Minneapolis, Minn.

[21] Appl. No.: 430,958

[22] Filed: Apr. 28, 1995

[51] Int. Cl.$^6$ .............. A61M 11/00; A61M 5/32
[52] U.S. Cl. .............. 604/93; 604/175; 604/167
[58] Field of Search .............. 604/174, 175, 604/93, 115, 264, 280, 167; 128/DIG. 26

[56] References Cited

U.S. PATENT DOCUMENTS

| | | | |
|---|---|---|---|
| Re. 31,272 | 6/1983 | Pevsner | 604/28 |
| 3,310,051 | 3/1967 | Schulte | 604/175 |
| 3,941,119 | 3/1976 | Corrales | |
| 4,405,305 | 9/1983 | Stephen et al. | 604/175 |
| 4,613,324 | 9/1986 | Ghajar | 604/49 |
| 4,705,501 | 11/1987 | Wigness et al. | 604/175 |
| 4,781,693 | 11/1988 | Martinez et al. | 604/175 |
| 4,784,638 | 11/1988 | Ghajar et al. | 604/49 |
| 4,795,426 | 1/1989 | Jones | 604/174 |
| 4,813,934 | 3/1989 | Engelson et al. | 604/99 |
| 4,863,438 | 9/1989 | Gauderer et al. | 604/175 |
| 4,884,579 | 12/1989 | Engelson | 128/772 |
| 4,931,056 | 6/1990 | Ghajar et al. | 606/130 |
| 4,955,862 | 9/1990 | Sepetka | 604/164 |
| 4,970,926 | 11/1990 | Ghajar et al. | 83/468.94 |
| 5,053,013 | 10/1991 | Ensminger et al. | 604/167 |
| 5,057,084 | 10/1991 | Ensminger et al. | 604/175 |
| 5,135,494 | 8/1992 | Engelson et al. | 604/99 |
| 5,180,365 | 1/1993 | Ensminger et al. | 604/175 |
| 5,180,387 | 1/1993 | Ghajar et al. | 604/266 |
| 5,213,570 | 5/1993 | VanDeripe | 604/28 |
| 5,217,484 | 6/1993 | Marks | 606/200 |
| 5,263,930 | 11/1993 | Ensminger | 604/175 |
| 5,300,080 | 4/1994 | Clayman et al. | 606/130 |
| 5,304,171 | 4/1994 | Gregory et al. | 606/15 |
| 5,312,356 | 5/1994 | Engelson et al. | 604/164 |
| 5,556,381 | 9/1996 | Ensminger et al. | 604/175 |

*Primary Examiner*—Mark Polutta
*Attorney, Agent, or Firm*—Curtis D. Kinghorn; Harold R. Patton

[57] ABSTRACT

A permanently implantable guiding catheter for facilitating access to a body tissue site in a patient. The guiding catheter has a substantially hollow cylindrical configuration, and has a port assembly including a self-sealable septum disposed on its proximal end. The guiding catheter is made of a biocompatible material such that it may be implanted with its distal end situated at the desired body tissue site and with its proximal end and port assembly subcutaneously disposed. In accordance with one aspect of the invention, the guiding catheter has sufficient inner diameter to allow passage of a flexible elongate medical instrument, such as a drug infusion catheter or the like, therethrough. An introducer needle is used to percutaneously pierce the septum. Then, the medical instrument is inserted into the needle such that its distal end is guided by the guiding catheter to the desired body tissue site. At the completion of a procedure, the medical instrument is withdrawn from the patient, leaving the guiding catheter in place.

15 Claims, 3 Drawing Sheets

PERMANENTLY IMPLANTABLE GUIDING CATHETER

FIELD OF THE INVENTION

This invention relates generally to the field of caterers, and more particularly to a permanently implantable guiding catheter for facilitating access to body tissue.

BACKGROUND OF THE INVENTION

In current medical practice, there are numerous instances where therapeutic agents are delivered to a specific organ or tissue area within the patient's body. One example of this is the infusion of chemotherapy agents into a central vein on a recurring basis over a lengthy treatment period for treatment of malignant tumors. Without an infusion device for intravenous drug infusion, multiple vein punctures over a lengthy period can result in progressive thrombosis, venous sclerosis, and destruction of small-diameter peripheral vessels. In other cases, it may be desired to infuse chemotherapy agents or other substances to a localized site, for example, to brain or liver tissue. In these situations, it can be difficult to deliver an agent specifically to such a localized site on a regular, repetitive basis without surgically implanting or otherwise introducing an infusion system.

Similarly, repeated arterial access is occasionally needed for injection of substances like X-ray dye or contrast agents into an artery for diagnostic purposes. In other situations, there is a need to remove body fluid repetitively from a remote body site, for analysis. Sensing and physiological measuring devices incorporated into small-diameter catheters and small-diameter optical fibers are increasingly being utilized for monitoring body processes, and could more easily be implemented through an access device with an adequate internal diameter.

In the prior art, it has been common medical practice to use percutaneous catheters for providing vascular or organ access for drag therapy or removing body fluids. Although such systems generally function in a satisfactory manner, numerous problems have been perceived by such approaches, including the substantial patient care requirements—e.g., dressing changes with sterile techniques—the significant risk of infection of the catheter due to its transcutaneous position, and the high risk of venous thrombosis, particularly if the catheter is located within an extremity vein.

Implantable infusion devices or "ports" have been proposed in the prior art as representing an advance over transcutaneous catheters. Presently available infusion ports have a number of common design features. The ports themselves typically comprise a housing which forms a reservoir which can be constructed from a variety of materials. A surface of the reservoir is enclosed by a high-density, self-sealing septum, typically made of silicone rubber. Connected to the port housing is an outflow catheter which communicates with a vein or other site within the patient where it is desired to infuse a therapeutic agent or to which access is otherwise necessary. Implantation of such devices generally involves making a small subcutaneous pocket in the patient under local anesthesia. The internal outflow catheter is tunneled to the desired infusion site and is connected to the infusion port. When the physician desires to access the site, for example, to infuse or remove material through the port, a hypodermic needle is used to pierce the skin over the port, and to pierce the septum.

Although presently available infusion systems have generally been deemed satisfactory, there are a number of potential shortcomings in practical application. Since these devices rely upon a compressed rubber septum for sealing, there can be limitations on the diameter of needles used to penetrate the septum, (large diameter needles can damage the septum and hinder proper sealing of the port). Moreover, the needles used for this purpose must be of special design which minimizes septum damage. These limitations can seriously restrict the flow rate of fluids passing through the port.

For prolonged infusion using a conventional port, the infusion needle may be taped to the patient's skin to hold it in position. Conventional ports do not allow the needle to penetrate deeply into the port, leading to the possibility that a small displacement of the needle can cause it to be pulled from the port. In cases where locally toxic materials are being infused, extravasation of such materials can cause local tissue damage making corrective surgery, e.g., skin grafting, necessary.

A further perceived disadvantage of prior art infusion ports is that they can be difficult to clear if thrombosis occurs within them or within the implanted outflow catheter, since it can be difficult to feed a cleaning wire through the penetrating hypodermic needle in a manner which will clear the infusion device and internal outflow catheter. Moreover, prior infusion ports typically have had a retained volume beneath the self-sealing septum, increasing the volume of agent which must be administered to enable a desired quantity to reach the infusion site. This can also pose problems when a physician wishes to deliver different, potentially incompatible, agents to the same infusion site. In addition, when it is desired to withdraw body fluid from through the port, the retained volume of prior art infusion ports is an area where blood clotting can occur, thus interfering with future access to the infusion site. Also, withdrawing fluid can require a large volume to fill the catheter and ports.

The introduction of infusion port and catheter systems as described above into the ventricular system of the human brain forms a large part of modern neurosurgical clinical practice. Procedures which involve the introduction of ventricular catheters include intracranial pressure monitoring, draining or shunting of cerebral-spinal fluid, and the infusion of pharmacological therapeutic agents. Catheters are also commonly introduced to access the heart, liver, subarachnoid space, or peritoneum.

Catheters can be introduced and positioned using a variety of standard surgical techniques, including direct observation, observation with imaging systems, and stereotactic placement., Each of the known techniques relies heavily upon the skill of the surgeon, and are relatively expensive and time-consuming. In the case of neurological catheter introduction, which is usually preceded by a CT scan or other imaging, the neurosurgeon first forms a burr hole in the skull, and then guides the catheter through the hole toward landmarks on the opposite side of the head. It is necessary that the neurosurgeon be able to accurately visualize the internal tomography of the brain when performing such a procedure, and it is presumed that the catheter is properly located when fluid is returned through the catheter. In some cases, however, the surgeon desires to check the location of the catheter, typically by subjecting the patient to another CT scan in order to verify proper location of the catheter. This can be costly, time consuming, and inconvenient.

Stereotactic placement of neurological catheters is generally regarded as an acceptable method of introducing neurological instruments. See, e.g., U.S. Pat. No. 5,300,080 to Clayman eta., entitled "Stereotactic Instrument Guide Placement." Stereotactic placement involves the use of an apparatus adapted to direct the neurological instrument, e.g., catheter, in three planes, to reach a specific site within the brain. A stereotactic procedure is a long and expensive operation. As such, it may not always be practical or desirable to perform the procedure multiple times on the same patient.

Stereotactic procedures may not be suitable for placement of extremely delicate neurological instruments which could be damaged by the stereotactic frame. In addition, stereotactic procedures cannot typically be used for placement of small diameter instruments or instruments which cannot accept a stiffening guide wire therein.

A further consideration with regard to the introduction of catheter and infusion port systems into a patient relates to the material from which the catheter is made. On the one hand, it is typically desirable for a catheter to be relatively thin and flexible; of course, the catheter material must also be compatible with the tissue in which it is intended to be implanted. On the other hand, however, the catheter material is preferably strong, particularly if stereotactic placement is used. In addition, the catheter must be compatible with whatever agent is to be conducted through it. Sometimes, the forgoing factors come into conflict. For example, a catheter material which is biocompatible with brain tissue, for example, might not be compatible with the drugs to be introduced with the catheter. Similarly, a material that is suitably flexible and thin may not be rugged enough to withstand the placement procedure.

The fact that few if any biocompatible materials are compatible with all drugs and other agents that may be introduced into a patient by means of a catheter can complicate situations in which it is desired to deliver multiple agents serially into a patient. One solution to this dilemma is to introduce a separate catheter for each agent to be delivered. This may not be acceptable or practical, however, particularly in view of the complexities of catheter introduction and the difficulties associated with achieving the desired placement of the catheter, as previously discussed.

SUMMARY OF THE INVENTION

In view of the foregoing considerations, the present invention is directed to a method and apparatus for performing surgical techniques, such as drug infusion, which conventionally involve the introduction of a catheter into a patient's body.

In accordance with one aspect of the present invention, a guiding catheter is permanently implanted in a patient's body. The guiding catheter can be positioned using conventional surgical techniques, including direct observation, observation by imaging systems, and/or stereotactic placement. The guiding catheter is made of biocompatible material and is preferably radiopaque. The guiding catheter may also be made of a material that is detectable during a nuclear magnetic resonance (NMR) imaging procedure.

In accordance with another aspect of the present invention, a needle or introducer is used to access the guiding catheter. The needle or introducer is placed through the skin and into a reseatable septum disposed on the proximal end of the guiding catheter. Once the needle or introducer is in place, another catheter, for example a drug infusion catheter, can be inserted through the needle or introducer, into the guiding catheter, and then to the target site.

In accordance with still another aspect of the invention, the permanently implanted guiding catheter can be used to guide catheters and other instruments to various sites in the body. For neurological applications, the guiding catheter in accordance with the present invention is designed for placement using a stereotactic frame. The guiding catheter is constructed from a material that is strong enough to withstand stereotactic placement and not be damaged during the surgical procedure, and which is biocompatible with brain tissue. Advantageously, compatibility with various drugs or other agents is not necessary for the guiding catheter, through which another catheter, for example a drug infusion catheter, extends during subsequent catheterization procedures.

In one embodiment of the invention, a permanently implanted guiding catheter is used as a guide for temporary drug infusion catheters and the like. For example, chemotherapy agents may be delivered periodically to a site at which the guiding catheter's distal end is positioned. In this embodiment, an access port is disposed upon the proximal end of the guiding catheter. The access port can be placed either in the skull or further down the body, at the neck or chest.

The guiding catheter in accordance with the present invention is preferably implanted once during a single surgical procedure using any conventional catheter insertion technique, such as stereotactic placement. Once the distal tip of the guiding catheter is confirmed to be accurately placed at the desired site, a drug infusion catheter may thereafter inserted into the guiding catheter, by accessing the septum of the access port with a needle introducer. The drug infusion catheter may be advanced through the guiding catheter to be guided to the desired site at the distal end of the guiding catheter. After drug is infused for the desired period of time, the drug infusion catheter is removed, leaving the guiding catheter in place for subsequent use.

The guiding catheter in accordance with the present invention allows for multiple agents to be used at different times for the same infusion site. This eliminates one problem with prior art catheter configurations, namely that few if any catheter materials are compatible with all agents.

In accordance with another aspect of the invention, a permanently implanted guiding catheter can serve as a surgical aid for permanently implanted systems, for example, an implanted pump or access port.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein.

DETAILED DESCRIPTION OF A SPECIFIC EMBODIMENT OF THE INVENTION

Figure 1:
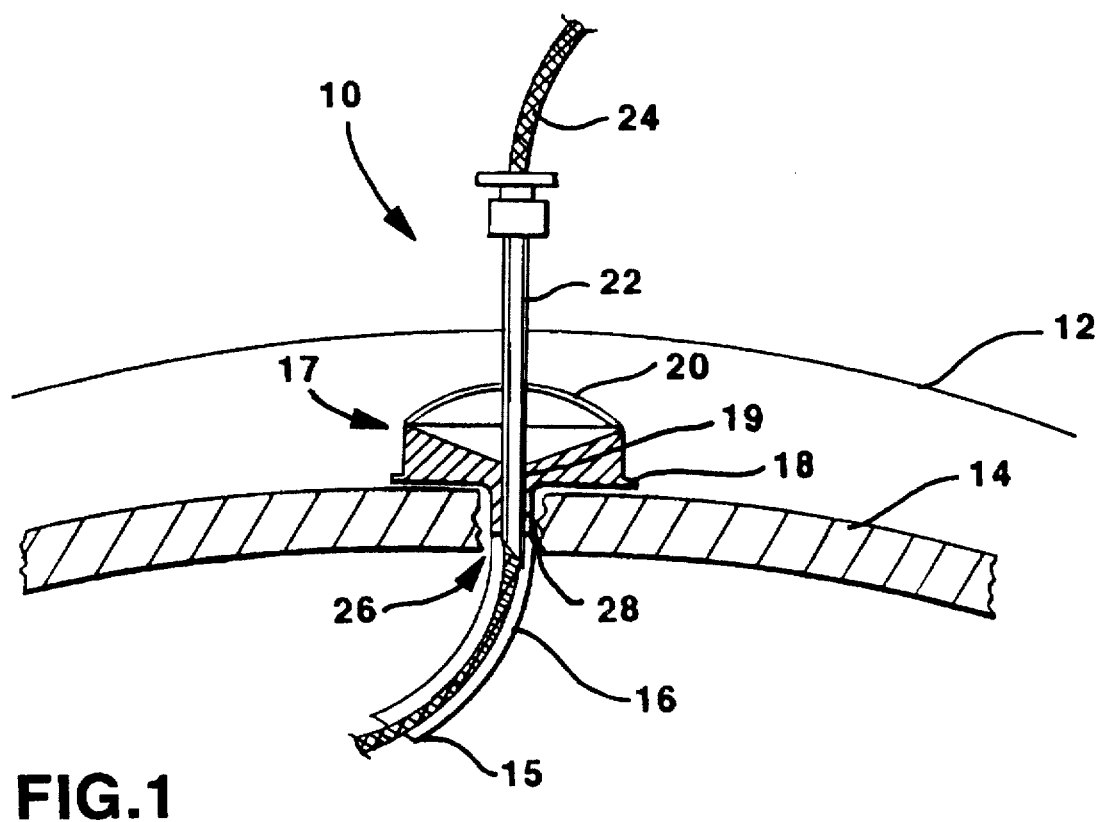
FIG. 1 is a cross-sectional view of a guiding catheter and port assembly in accordance with one embodiment of the invention, implanted in a patient and having an introducer needle percutaneously piercing the port assembly.

Referring to FIG. 1, there is shown an enlarged cross-sectional view of a permanently implantable catheter/port assembly 10 in accordance with one embodiment of the invention. In FIG. 1, catheter/port assembly 10 is shown having been implanted under a patient's skin 12, extending through the patient's skull 14 such that the distal end 15 of a guiding catheter portion 16 is situated at a desired site within the patient's cranial cavity. Although the present invention will be described herein in connection with a catheter/port assembly 10 suitable for cranial implantation in support of neurological treatment of the patient, it is contemplated that the present invention may be advantageously practiced in connection with catheter/port assemblies useful at other locations on the body, for example, for catheters providing access to liver tissue, heart tissue, or the like.

In addition to guiding catheter 16, catheter/port assembly 10 comprises an access port 17 having a base portion 18 with a cylindrical central opening 19 and a sealing cap or dome 20. Dome 20 acts as a septum to prevent body fluids from entering catheter/port assembly 10. In the presently preferred embodiment of the invention, cap 20 is made of an elastomeric material such as silicone rubber or the like, that it is capable of self-sealing around an introducer needle 22 of sufficient diameter to allow passage of an infusion catheter or other elongate medical instrument 24 therethrough.

Guiding catheter 16 has a tubular configuration, and is preferably made of a biocompatible material having a slippery surface, for example, PTFE. (Materials and methods for providing a suitably low-friction catheter are proposed, for example, in U.S. Pat. No. 5,312,356 to Engelson et al., entitled "Catheter With Low Friction Distal Segment.") Base portion 18 of port 17 is preferably made of a rigid, biocompatible material, such as titanium or polysulfone.

In use, cranial implantation of catheter/port assembly 10 begins with formation of a burr hole 26 in skull 14, in accordance with conventional neurosurgical practice. (A method and apparatus for drilling a burr hole in a human cranium is proposed, for example, in U.S. Pat. No. 4,931, 056 to Ghajar et al.) Next, guiding catheter 16 is inserted until its distal end 15 is disposed at the desired location, using a stereotactic frame, such as disclosed in the above-referenced Clayman et al. '080 patent, or as proposed in U.S. Pat. No. 4,613,324 to Ghajar et al., entitled "Method and Apparatus for Guiding Catheter Into Ventricular System of Human Brain."

Once guiding catheter 16 is inserted, access port 17 is attached to the proximal end thereof, and placed substantially outside skull 14 (although an annular collar portion 28 of port 17 may extend into burr hole 26, as shown in FIG. 1). The skin 12 is then closed on top of port 17, ending the surgical implantation procedure. Friction between infusion catheter 24 and dome 20 retains infusion catheter 24 in place.

To utilize catheter/port assembly 10 in accordance with the presently preferred embodiment of the invention, for example, to infuse a drug or other agent, cap 20 of access port 17 is penetrated by introducer needle 22. As shown in FIG. 1, needle 22 is preferably of sufficient diameter to allow passage of an elongate instrument, such as infusion catheter 24, therethrough.

Figure 2:
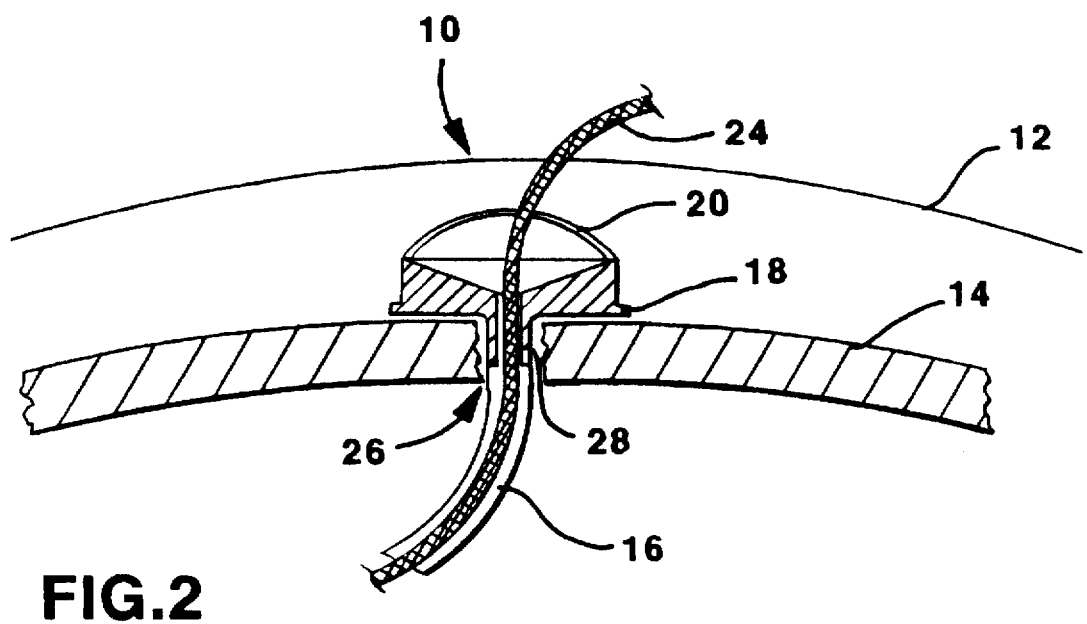
FIG. 2 is a cross-sectional view of the guiding catheter and port assembly from FIG. 1 having an elongate medical instrument extending therethrough.

Once catheter 24 has been guided to the desired infusion site, needle 22 may be removed by drawing it out from cap 20. (To this end, needle 22 may be of the splittable type, as is well-known in the art, to facilitate removal thereof from catheter 24 without the necessity of drawing needle 22 past the proximal end of catheter 24.) Cap 20 then self-seals around catheter 24, as shown in FIG. 2. Drug may then be infused at the desired site using infusion catheter 24 in a conventional manner. After the infusion procedure, catheter 24 is withdrawn from catheter/port assembly 10. In accordance with one advantageous aspect of the present invention, however, the infusion procedure, or any other procedure requiring access to the same site, may be repeatedly performed without the necessity of repeated stereotactic implantation procedures.

In the preferred embodiment, distal end 15 of guiding catheter 16 is open. Body fluids will not enter guiding catheter 16 through distal end 15 if dome 20 is intact. It may be desirable to add a sealing mechanism to distal end 15 to ensure that body fluid will not enter guiding catheter 16 even if dome 20 is no longer intact.

Figure 3:
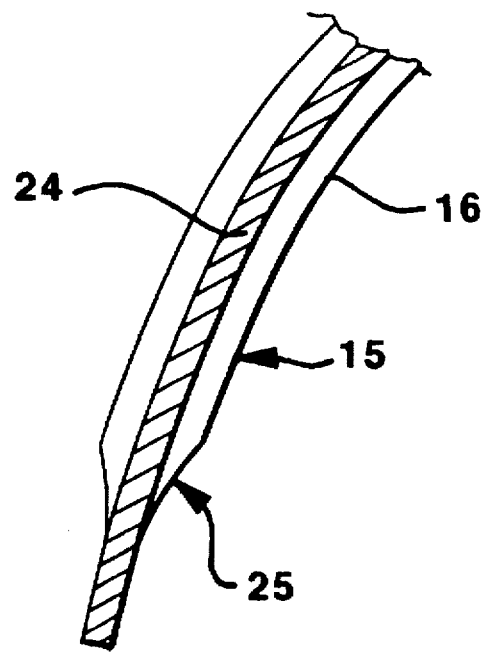
FIG. 3 is a cross-sectional view of the distal end of the guiding catheter with a sealing valve attached and with an infusion catheter within the guiding catheter.
Figure 4:
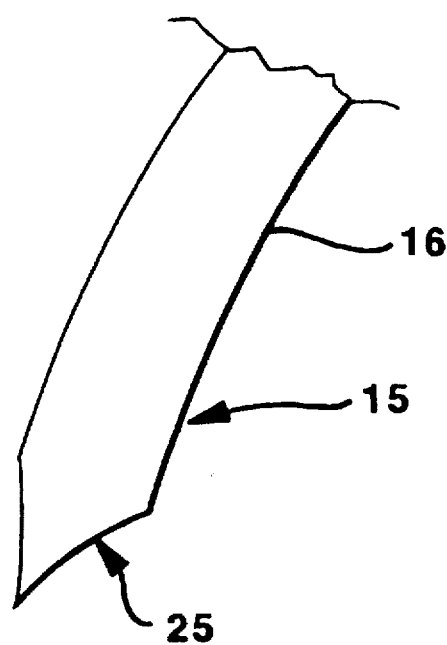
FIG. 4 is a cross-sectional view of the distal end of the guiding catheter with a sealing valve attached of FIG. 3 and with the infusion catheter removed from within the guiding catheter.

FIGS. 3 and 4 show distal end 15 with a sealing valve 25 attached thereto. In the preferred embodiment, sealing valve 25 is a "duck-bill" type valve although other types of sealing valves may be used. Examples of such valves include, but are not limited to, a movable diaphragm and multiple leaf valve. FIG. 3 shows distal end 15 with sealing valve 25 attached thereto and infusion catheter 22 extending through sealing valve 25. As can be seen, sealing valve 25 provides a seal around infusion catheter 22 so that body fluids may not enter guiding catheter 16 by bypassing sealing valve 25.

FIG. 4 shows the same distal end 15 with sealing valve 25 of FIG. 3, but with infusion catheter 22 removed. As can be seen, with infusion catheter 22 removed, sealing valve 25 closes so that no body fluids may enter guiding catheter 16 by bypassing sealing valve 25. By using sealing valve 25, even when no infusion catheter 22 is present to inhibit the passage of body fluid into guiding catheter 16, body fluid is prevented from entering guiding catheter 16. As a result, even if dome 20 is not intact, body fluid will not enter guiding catheter 16.

As described above, frictional contact between infusion catheter 24 and dome 20 retains infusion catheter 24 in place. However, some materials for infusion catheter 24 may have a low coefficient of friction. Consequently, the frictional contact between infusion catheter 24 and dome 20 may not be sufficient to retain infusion catheter 24 in place. When these materials are used for infusion catheter 24, it is preferable to include a positive locking mechanism to retain infusion catheter 24 in place.

Figure 5:
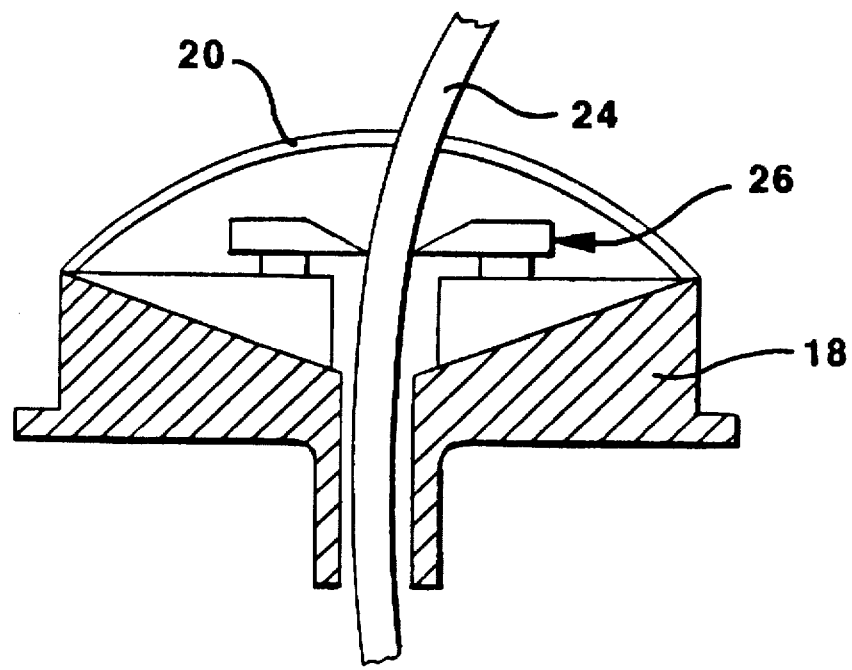
FIG. 5 is a cross-sectional view of the guiding catheter and port assembly of FIGS. 1 and 2 with a positive locking mechanism in place within the guiding catheter and port assembly and with an infusion catheter extending through the positive locking mechanism.
Figure 6:
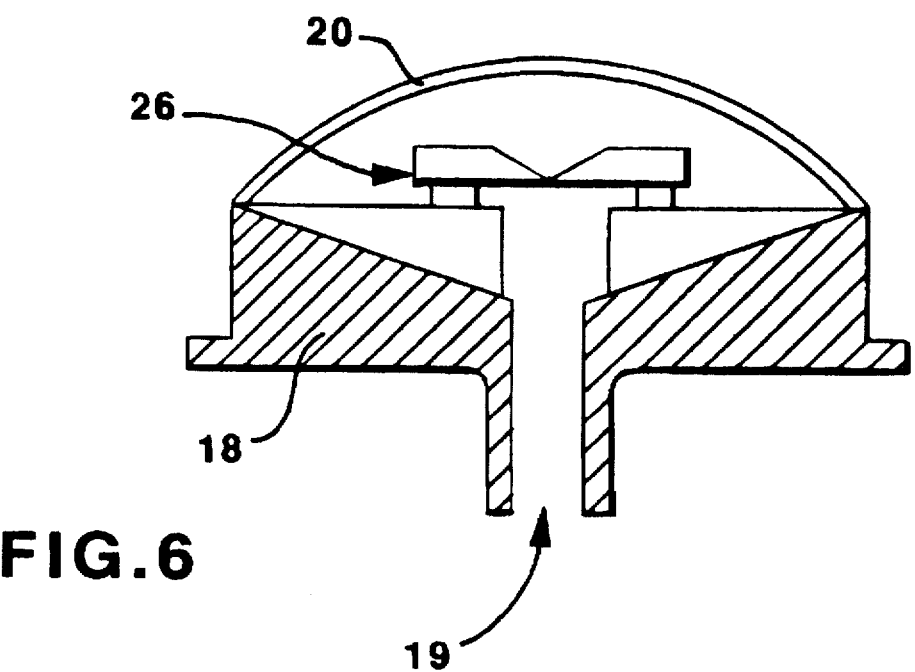
FIG. 6 is a cross-sectional view of the guiding catheter and port assembly of FIGS. 1 and 2 with a positive locking mechanism of FIG. 5 with the infusion catheter removed from extending through the positive locking mechanism.

FIGS. 5 and 6 show an example of the catheter/port assembly incorporating a positive locking mechanism to retain infusion catheter 24 in place. The preferred positive locking mechanism is a spring loaded latch 26. Spring loaded latch 26 is preferably located within dome 20 on base 18 and is concentric with central opening 19.

As shown in FIG. 5, when an object such as an introducer needle 22 containing infusion catheter 24 comes in contact with spring loaded latch 26, spring loaded latch 26 opens to allow introducer needle 22 to pass into central opening 19. After the distal end 15 of guiding catheter 16 has been positioned, introducer needle 22 is removed leaving infusion catheter 24 in place in the patient's cranium and extending through catheter/port assembly 10.

The bias of the spring on spring loaded latch 26 grips the outer surface of infusion catheter 24 and with the frictional contact supplied by dome 20, retains infusion catheter 24 in position. When introducer needle 22 is removed, spring loaded latch 26 closes, as shown in FIG. 6. To remove infusion catheter 24, introducer needle 22 is applied over infusion catheter 24 to open spring loaded latch 26 so that infusion catheter 24 can be removed.

From the foregoing detailed description of a specific embodiment of the invention, it should be apparent that a method and apparatus for permanently implanting a guiding catheter in a patient has been disclosed. Although a specific embodiment of the invention has been described herein in some detail, this has been done solely for the purpose of illustrating the invention in various of its aspects, and is not intended to be limiting with respect to the scope of the invention. It is contemplated that a person of ordinary skill in the art having the benefit of the present disclosure may make various alterations, substitutions, and/or modifications, including but not limited to those specifically noted herein, without departing from the spirit and scope of the invention as defined in the appended claims, which follow.

What is claimed is:

1. A permanently implantable guiding catheter for facilitating repeated access to a body tissue site, the guiding catheter comprising:

a flexible, elongate catheter body having a substantially hollow cylindrical configuration, the catheter body having a proximal end, and having an openable distal end adapted to be disposed generally at the body tissue site, the distal end having a seal;

a port assembly, coupled to the proximal end of the catheter body, for retaining the catheter body in position, the port assembly including a self-sealable septum for preventing seepage of body fluids into the catheter body or from the openable distal end of the catheter body into the adjacent subcutaneous tissue, the port assembly adapted to be subcutaneously disposed;

wherein the catheter body has a sufficient internal diameter to allow passage of a flexible elongate medical instrument therethrough, such that a distal end of the medical instrument is provided access to the body tissue site through the seal of the distal end of the catheter body.

2. A guiding catheter in accordance with claim 1, wherein the medical instrument is a drug infusion catheter.

3. A guiding catheter in accordance with claim 1, wherein the guiding catheter is made of PTFE.

4. A guiding catheter in accordance with claim 1, wherein the self-sealable septum is made of silicone rubber.

5. A guiding catheter in accordance with claim 1, wherein the body tissue site is located in the patient's epidural space, intrathecal space or cranium, including but not limited to the ventricles of the brain or brain tissue.

6. A guiding catheter in accordance with claim 1, wherein the catheter body is made of a material that is biocompatible.

7. A guiding catheter in accordance with claim 1, wherein the catheter body is made of a material that is radiopaque.

8. A guiding catheter in accordance with claim 1, wherein the catheter body is made of a material that is detectable by a nuclear magnetic resonance (NMR) device during a nuclear magnetic resonance procedure.

9. A guiding catheter in accordance with claim 1, wherein the seal comprises a sealing valve attached to the distal end of the catheter body to prevent body fluids from entering the catheter body.

10. A guiding catheter in accordance with claim 1, wherein the port assembly includes a base portion with a central opening extending therethrough for receiving a medical device.

11. A guiding catheter in accordance with claim 1, wherein the self-sealable septum comprises a dome made of an elastomeric material.

12. A guiding catheter in accordance with claim 1, further comprising a positive locking mechanism for retaining the medical instrument in the catheter body.

13. A permanently implantable guiding catheter for facilitating repeated access to a body tissue site, the guiding catheter comprising:

a flexible, elongate catheter body having a substantially hollow cylindrical configuration, the catheter body having a proximal end, and having an openable distal end adapted to be disposed generally at the body tissue site, the distal end having a sealing valve attached to the distal end of the catheter body to prevent body fluids from entering the catheter body;

a port assembly, coupled to the proximal end of the catheter body, for retaining the catheter body in position, the port assembly including a base portion with a central opening extending therethrough for receiving a medical device and a self-sealable septum for preventing seepage of body fluids into the catheter body or from the openable distal end of the catheter body into the adjacent subcutaneous tissue, the self-sealable septum comprising a dome made of an elastomeric material, the dome attached to and extending over the base to cover the central opening in the base, the port assembly adapted to be subcutaneously disposed;

wherein the catheter body has a sufficient internal diameter to allow passage of a flexible elongate medical instrument therethrough, such that a distal end of the medical instrument is provided access to the body tissue site through the sealing valve.

14. A system for facilitating repeated access to a body tissue site, the system comprising:

a guiding catheter comprising:
      a flexible, elongate catheter body having a substantially hollow cylindrical configuration, the catheter body having a proximal end, and having an open distal end adapted to be disposed generally at the body tissue site;
      a port assembly, coupled to the proximal end of the catheter body, for retaining the catheter body in position, the port assembly including a self-sealable septum for preventing seepage of body fluids into the catheter body or from the open distal end of the catheter body into the adjacent subcutaneous tissue, the port assembly adapted to be subcutaneously disposed;
   a hollow needle to access the guiding catheter, the needle having a sharpened distal end to pass through the skin and into the septum of the port assembly;
   a flexible, elongate infusion catheter, the infusion catheter having a substantially hollow cylindrical configuration, the catheter body having a proximal end, and having an open distal end adapted to be disposed generally at the body tissue site;

wherein the guiding catheter body has a sufficient internal diameter to allow passage of the needle therethrough;

wherein the needle has a sufficient internal diameter to allow passage of the infusion catheter therethrough, such that a distal end of the infusion catheter is provided access to the body tissue site;

whereby, the guiding catheter is placed in position in a patient's body, the needle placed through the guiding catheter and the drug infusion catheter placed through the needle.

15. A system for facilitating repeated access to a body tissue site, the system comprising:

a guiding catheter comprising:

a flexible, elongate catheter body having a substantially hollow cylindrical configuration, the catheter body having a proximal end, and having a distal end adapted to be disposed generally at the body tissue site, the distal end having a seal;

a port assembly, coupled to the proximal end of the catheter body, for retaining the catheter body in position, the port assembly including a self-sealable septum for preventing seepage of body fluids into the catheter body or from the open distal end of the catheter body into the adjacent subcutaneous tissue, the port assembly adapted to be subcutaneously disposed;

a flexible, elongate infusion catheter, the infusion catheter having a substantially hollow cylindrical configuration, the catheter body having a proximal end, and having an open distal end adapted to be disposed generally at the body tissue site;

wherein the guiding catheter body has a sufficient internal diameter to allow passage of the infusion catheter therethrough, such that a distal end of the infusion catheter is provided access to the body tissue site;

whereby, the guiding catheter is placed in position in a patient's body and the drug infusion catheter placed through the guiding catheter to the body tissue site through the seal of the distal end of the catheter body.

\* \* \* \* \*